United States Patent [19]

Czerney et al.

[11] 4,417,060
[45] Nov. 22, 1983

[54] AMINO-SUBSTITUTED 2-CUMARYL-(3)-CHROMENYLIUM SALTS

[75] Inventors: Peter Czerney, Weimar; Horst Hartmann; Jürgen Liebscher, both of Dresden, all of German Democratic Rep.

[73] Assignee: Jenoptik Jena GmbH, Jena, German Democratic Rep.

[21] Appl. No.: 247,954

[22] Filed: Mar. 26, 1981

[30] Foreign Application Priority Data

Apr. 1, 1980 [DD] German Democratic Rep. ... 220109

[51] Int. Cl.³ .......................................... C07D 405/14
[52] U.S. Cl. .................................. 548/525; 548/518; 549/280; 549/288; 549/289; 549/290; 430/82; 430/83
[58] Field of Search ............... 549/288, 289, 290, 280; 548/525, 518

[56] References Cited

U.S. PATENT DOCUMENTS 3,907,561  9/1975  Kubota ................................ 549/289

*Primary Examiner*—Jane T. Fan
*Attorney, Agent, or Firm*—Jordan and Hamburg

[57] ABSTRACT

The present invention is directed to novel amino-substituted 2-cumaryl-3'-chromenylium salts of the general formula

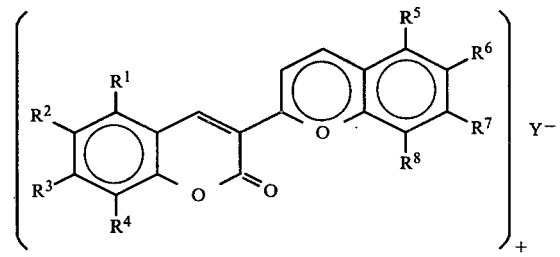

wherein $R^3$ and $R^7$ are a dialkyl or cycloalkyl disubstituted amino group, hydrogen, or hydroxy group, provided that at least one of $R^3$ and $R^7$ is an amino group, $R^1$, $R^2$, $R^4$, $R^5$, $R^6$, and $R^8$ are hydrogen, an alkoxy group, or two of these substituents together form an aromatic ring, provided that $R^1$, $R^2$ and $R^4$ may be the same or different, and $R^5$, $R^6$ and $R^8$ may be the same or different, and $Y^-$ is an acidic anion and to the process for their preparation.

11 Claims, No Drawings

AMINO-SUBSTITUTED 2-CUMARYL-(3)-CHROMENYLIUM SALTS

BACKGROUND OF THE INVENTION AND PRIOR ART STATEMENT

The invention relates to a process for the preparation of amino-substituted 2-cumaryl-(3')-chromenylium salts. Compounds of this kind are important as dyestuffs, especially in copying processes and, in electrophotography.

According to the state of the art, a method for the preparation of 2-cumaryl-(3')-chromenylium salts is known (DE-OS No. 2,349,960) but it relates only to the preparation of 2-cumaryl-(3')-chromenylium salts which do not possess any amino-functional groups.

Amino-substituted 2-cumaryl-(3')-chromenylium salts have previously not been known.

The object of the invention is to prepare previously unknown amino-substituted 2-cumaryl-(3')-chromenylium salts in an uncomplicated manner.

SUMMARY OF THE INVENTION

The task of the invention is to synthesize the previously unknown amino-substituted 2-cumaryl-(3')-chromenylium salts by using simply produced starting materials. The task is solved according to the invention by reacting substituted 3-acetylcumarines of type I

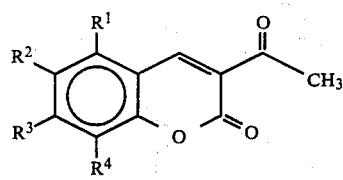

in the presence of an acid HY with substituted salicylaldehydes of type II

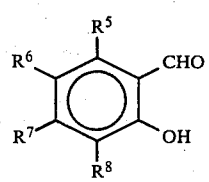

or by reacting 3-chloro-3-cumaryl-(3')-propene-(2)-iminium salts or -aldehydes of type III, respectively

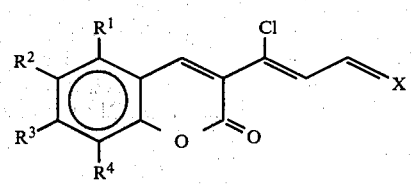

where X denotes an oxygen atom or an iminium salt group, in the presence of an acid HY with substituted phenols of type IV

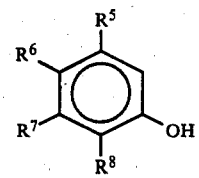

so that amino-substituted 2-cumaryl-(3')-chromenylium salts of Type V

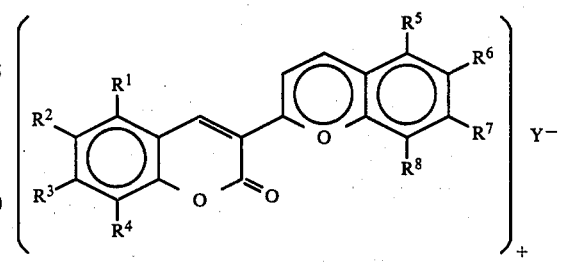

result, where $R^3$ and/or $R^7$ are a dialkyl or cycloalkyl-disubstituted amino group, hydrogen or a hydroxy group, and where $R^1$, $R^2$ and $R^4$ as well as $R^5$, $R^6$ and $R^8$ may be the same or different and are hydrogen, one alkoxy group or two of these substituents together form an aromatic ring and where $Y^-$ is an acid radical as for instance $ClO_4^-$.

DETAILED DESCRIPTION OF PREFERRED EMBODIMENTS

The invention will be explained infra by using the amino-substituted 2-cumaryl-(3')-chromenylium salts, listed in the appended tables as examples of execution which were prepared according to the following variations:

Variant A 0.01 Mol 3-acetyl curmarin of type I is mixed with 25 ml glacial acetic acid, 2 ml perchloric acid (70%) and 0.01 Mol substituted salicylaldehyde of type II. The mixture is heated 25 minutes to gentle boiling. The chromenylium compound of Type V precipitates on cooling, is suctioned off and recrystallized.

Variant B

The sequence is analogous to variant A except that 15 ml acetic anhydride are used instead of glacial acetic acid and the mixture is heated only 10 minutes to a gentle boil.

Variant C 0.01 Mol of acetylcumarin of type I and 0.01 Mol substituted salicylaldehyde of type II are dissolved in 20 ml 85% formic acid. Thereafter, hydrogen chloride is bubbled through for 5 hours at room temperature. After consecutively adding 100 ml glacial acetic acid and 30 ml 20% perchloric acid, the chromenylium compound of type V is precipitated by water, suctioned off and recrystallized.

Variant D 0.01 Mol 3-chloro-3-cumaryl-(3')-propene-(2)-iminium salt of type III (X=$_N^+$(CH$_3$)$_2$ClO$_4^-$), prepared according to WP C 07 D/209 424 and 0.01 Mol of a substituted phenol of type IV are suspended in 20 ml glacial acetic acid and heated under reflux for one hour. Thereafter, 2 ml 70% perchloric acid is carefully added, and the immediately occurring precipitate of the chromenylium compound of type V is suctioned and recrystallized.

Variant E

The sequence is analogous to variant D except that 15 ml acetone hydride is used and the mixture is heated only 10 minutes to boiling.

Variant F

The sequence is analogous to variant D but instead of using 3-chloro-3-cumaryl-(3')-propene-(2)-iminium salts, the 3-chloro-3-cumaryl-(3')-propene-(2)-aldehydes of type III (X=O) are used, prepared according to WP C07 D/209 424.

The examples of execution listed in the table are compounds which were recrystallized from glacial acetic acid. The melting points in all cases lie above 360° C.

$R^1$, $R^2$, $R^4$, $R^5$, $R^6$, and $R^8$ are hydrogen, an alkoxy group, or two of these substituents together form an aromatic ring, provided that $R^1$, $R^2$ and $R^4$ may be the same or different, and $R^5$, $R^6$ and $R^8$ may be the same or different, and $Y^-$ is an acidic anion.

2. The amino-substituted 2-cumaryl-3'-chromenylium salt of claim 1 wherein $R^1$–$R^6$ and $R^8$ are hydrogen and $R^7$ is N-pyrolidinyl-.

3. The amino-substituted 2-cumaryl-3'-chromenylium salt of claim 1 wherein $R^1$ and $R^2$ together form (—CH=CH—)$_2$, $R^3$–$R^6$ and $R^8$ are hydrogen, and $R^7$ is N-pyrolidinyl-.

4. The amino-substituted 2-cumaryl-3'-chromenylium salt of claim 1 wherein $R^1$, $R^2$ and $R^4$–$R^8$ are hydrogen, and $R^3$ is N-pyrolidinyl-.

5. The amino-substituted 2-cumaryl-3'-chromenylium salt of claim 1 wherein $R^1$, $R^2$, $R^4$, $R^7$ and $R^8$ are hydrogen, $R^3$ is N-pyrolidinyl-, and $R^5$ and $R^6$ together form (—CH=CH—)$_2$.

6. The amino-substituted 2-cumaryl-3'-chromenylium

Table showing prepared amino substituted 2-cumaryl-(3')-chromenylium salts of type V ($Y^-$=ClO$_4$)

| Example of Execution No. | $R^1$ | $R^2$ | $R^3$ | $R^4$ | $R^5$ | $R^6$ | $R^7$ | $R^8$ | λmax (lg ε) in acetonitrile | yield in % of theory/variant |
|---|---|---|---|---|---|---|---|---|---|---|
| 1 | —H | —H | —H | —H | —H | —H | N—Pyrolidinyl- | —H | 563 (4.41) | 86/A 57/D |
| 2 | (—CH=CH—)$_2$ | | —H | —H | —H | —H | N—Pyrolidinyl- | —H | 582 (4.39) | 91/A 77/F |
| 3 | —H | —H | N—Pyrolidinyl- | —H | —H | —H | —H | —H | 639 (4.78) | 81/A |
| 4 | —H | —H | N—Pyrolidinyl- | —H | —(CH=CH)—$_2$ | | —H | —H | 634 (4.91) | 94/A 78/E |
| 5 | —H | —H | N—Pyrolidinyl- | —H | —H | —H | —H | —OCH$_3$ | 613 (4.52) | 94/A |
| 6 | —H | —H | —N(CH$_3$)$_2$ | —H | —H | —H | —H | —OCH$_3$ | 605 (4.51) | 98/A |
| 7 | —H | —H | N—Pyrolidinyl- | —H | —H | —H | —OH | —H | 610 (4.94) | 91/A |
| 8 | —H | —H | —N(CH$_3$)$_2$ | —H | —H | —H | —N(CH$_3$)$_2$ | —H | 650 (4.86) | 89/A 87/B |
| 9 | —H | —H | —N(C$_2$H$_5$)$_2$ | —H | —H | —H | —N(C$_2$H$_5$)$_2$ | —H | 658 (4.95) | 83/A 71/C |
| 10 | —H | —H | N—Pyrolidinyl- | —H | —H | —H | N—Pyrolidinyl- | —H | 659 (4.89) | 92/A |

We claim:
1. Amino-substituted 2-cumaryl-3'-chromenylium salt of the formula

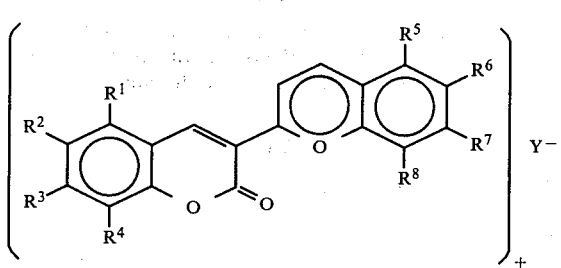

wherein $R^3$ and $R^7$ are a dialkyl or cycloalkyl disubstituted amino group, hydrogen, or hydroxy group, provided that at least one of $R^3$ and $R^7$ is an amino group, salt of claim 1 wherein $R^1$, $R^2$, and $R^4$–$R^7$ are hydrogen, $R^3$ is N-pyrolidinyl-, and $R^8$ is —OCH$_3$.

7. The amino-substituted 2-cumaryl-3'-chromenylium salt of claim 1 wherein $R^1$, $R^2$, and $R^4$–$R^7$ are hydrogen, $R^3$ is —N(CH$_3$)$_2$, and $R^8$ is —OCH$_3$.

8. The amino-substituted 2-cumaryl-3'-chromenylium salt of claim 1 wherein $R^1$, $R^2$, $R^4$–$R^6$, and $R^8$ are hydrogen, $R^3$ is N-pyrolidinyl-, and $R^7$ is —OH.

9. The amino-substituted 2-cumaryl-3'-chromenylium salt of claim 1 wherein $R^1$, $R^2$, $R^4$–$R^6$, and $R^8$ are hydrogen, and $R^3$ and $R^7$ are —N(CH$_3$)$_2$.

10. The amino-substituted 2-cumaryl-3'-chromenylium salt of claim 1 wherein $R^1$, $R^2$, $R^4$–$R^6$, and $R^8$ are hydrogen, and $R^3$ and $R^7$ are —N(C$_2$H$_5$)$_2$.

11. The amino-substituted 2-cumaryl-3'-chromenylium salt of claim 1 wherein $R^1$, $R^2$, $R^4$–$R^6$, and $R^8$ are hydrogen and $R^3$ and $R^7$ are N-pyrolidinyl-.

* * * * *